US007060792B2

(12) United States Patent
Oeltgen et al.

(10) Patent No.: US 7,060,792 B2
(45) Date of Patent: Jun. 13, 2006

(54) PROTECTION AGAINST ISCHEMIA AND REPERFUSION INJURY

(75) Inventors: Peter R. Oeltgen, Winchester, KY (US); Paul D. Bishop, Fall City, WA (US); Mark S. Kindy, Lexington, KY (US); Juan A. Sanchez, Waltham, MA (US)

(73) Assignees: University of Kentucky Research Foundation, Lexington, KY (US); Zymogenetics, Seattle, WA (US)

( * ) Notice: Subject to any disclaimer, the term of this patent is extended or adjusted under 35 U.S.C. 154(b) by 0 days.

(21) Appl. No.: 11/141,670

(22) Filed: May 31, 2005

(65) Prior Publication Data

US 2005/0222038 A1 Oct. 6, 2005

Related U.S. Application Data

(63) Continuation of application No. 09/947,656, filed on Sep. 6, 2001, now Pat. No. 6,900,178.

(60) Provisional application No. 60/232,093, filed on Sep. 12, 2000.

(51) Int. Cl.
*A61K 38/00* (2006.01)
(52) U.S. Cl. ..................................... 530/326
(58) Field of Classification Search .................. 514/13; 530/326
See application file for complete search history.

(56) References Cited

U.S. PATENT DOCUMENTS

| 5,656,420 A | 8/1997 | Chien ......................... 435/1.2 |
| 6,103,722 A | 8/2000 | Schultz et al. ............... 614/249 |

FOREIGN PATENT DOCUMENTS

| WO | WO 99/04795 | 2/1999 |
| WO | WO 99/56766 | 11/1999 |
| WO | WO 99/56767 | 11/1999 |

OTHER PUBLICATIONS

Mor et al. Isolation of dermenkephalin from amphibian skin, a high-affinity delta-selective opioid heptapeptide containing a D-amino acid residue. Febs Letters. Sep. 1989. vol. 255, No. 2, pp. 269-274.*
Fryer et al., *Opioid-Induced cardioprotection against myocardial infarction and arrhythmias: Mitochondrial versus sarcolemmal ATP sensitive potassium channels*, The Journal of Pharmacology and Experimental Therapeutics, 2000 234(2):451-457.
Lazarus et al., *Opioid infidelity: novel opioid peptides with dual high affinity for delta and mu receptors*, Trends in Neuroscience, 1996, 19:31-35.
Krell, G., *D-amino acids in animal peptides*, Annual Review of Biochemistry, 1997, 66:337-345.
Fryer et al., *Opioid-induced second window of cardioprotection: Potential role of mitochondrial K-ATP channels*, Circulation Research, 1999, 84:848-851.
Barra et al., *Deltorphin, a 17 amino acid opioid peptide from the sking of the Brazilian hylid frog, Phyilomedusa burmelsteri*, Peptides (Tarrytown), vol. 15, No. 2, 1994, 199-202.
Bohlinger et al., *Interleukin-1 and nitric oxide protect against tumor necrosis factor α-induced liver injury through distinct pathways*, Hepatology, 22: 1829-1837, 1995.
Bolling et al., *Delta opioid agonist/antagonist activity and ischemic tolerance*, American Heart Association Meeting, Atlanta, GA, Nov., 1999.
Bolling et al., *The use of hibernation induction triggers for cardiac transplant preservation*, Transplantation 63: 326-329, 1997.
Bolling et al., *Use of "natural" hibernation induction triggers for myocardial protection*, Annals Thorac. Surg.: 623-627, 1997.
Bolling et al., *Hibernation triggers and myocardial protection*, Cirulation 98: II220-II1224, 1998.
Chien et al., *Two-day preservation of major organs with autoperfusion multiorgan preparation and hibernation induction trigger*, J. Thorac. Cardiovasc. Surg., 102: 224-234, 1991.
Chien et al., *Extension of tissue survival time in multiorgan block preparation with a delta opioid DADLE (ID-Ala2, D-Leu51-enkephalin)*, J. Thorac. Cardiovasc. Surg., 107: 965-967, 1994.
Crain and Shen, *Antagonists of excitatory opiod receptor functions enhance morphine's analgesic potency and attenuate opioid tolerance/dependence liability*, Paln 84 (2000), 121-131.
Ersparner, et al.,, *Deltorphlns: A family of naturally occurring peptides with high affinity and selectivity for opioid binding sites*,, Proceedings of the National Academy of Sciences of the USA 86 (1989) Jul., No. 13, Washington, DC, US.

(Continued)

*Primary Examiner*—Robert A. Wax
*Assistant Examiner*—Suzanne M. Noakes
(74) *Attorney, Agent, or Firm*—Wood, Herron & Evans, L.L.P.

(57) ABSTRACT

A compound and method for using the compound to reduce injury associated with ischemia and reperfusion of mammalian organs such as the heart. The compound, either Deltorphin A and/or Dermorphin H, may be administered as part of a preconditioning strategy which reduces the extent of injury and improves organ function following cessation and restoration of blood flow. The compound may be used in preparation for planned ischemia or in a prophylactic manner in anticipation of further ischemic events.

1 Claim, 3 Drawing Sheets

OTHER PUBLICATIONS

Fryer et al., *Opioid-induced second window of cardioprotection: Potential role of mitochondrial K-ATP channels*, Circ Res. 1999; 84: 846-851.

House et al., *A comparative study of immunomodulation produced by in vitro exposure to delta opioid receptor agonist peptides*, Peptides, (1996) 17 (1): 75-61.

Kevelaitis et al., *Opening of potassuim channels: The common cardioprotective link between perconditioning and natural hibernation?*, Circulation 99: 3079-3085, 1999.

Leist et al., *Activation of the 55 kDA TNF receptor is necessary and sufficient for TNF-induced liver failure, hepatocyte apoptosis, and nitrite release*, The Journal of Immunology 154: 1307-1316, 1995.

Leist et al., *Murine hepatocyte apoptosis Induced in vitro and in vivo by TNF-α requires transcriptional arrest*, The Journal of Immunology, 153: 1778-1788, 1994.

Lishmanov et al., *Activation of the μ-opioid receptors as a factor increasing heart resistance aganist ischemic and reperfusion damages*, Russian J. Physiol. 1998, 84 (11) (Russian w/ attached English translation).

Malaguarnera et al., *Elevation of Interleukin 6 levels in patients with chronic hepatitis due to hepatitis C virus*, Journal of Gastroenterology, 32: 211-215, 1997.

Maslov and Lishrnanov, *Effects of μ- and delta opioid receptor ligands on rhythm and contractility disorders of isolated rat. heart in postischemic period*, Kardiologya 1998; 12: 25-30 (Russian w/ English translation).

Mayfield and D'Alecy, *Delta-1 opioid receptor dependence of acute hypoxic adaptation*, J. Pharmacol. Exp. Ther. 268: 74-77, 1994.

Morgan, *Regulation of human B lymphocyte activation by opioid peptide hormones: Inhibition of IgG production by opioid receptor class (gamma-kappa-, and delta) selective agonists*, Journal of Neuroimmunology, vol. 65, No. 1: 21-30, 1996.

Oeltgen et al, *The use of delta-2 opioid agonists for myocardial Ischemia protection*, Abstract, Experimental Biology 2000, submitted Nov., 1999.

Oeltgen et al., *Extended lung preservation with the use of hibernation trigger factors*, Ann. Thorac, Surg. 61: 1468-93, 1996.

Reisine et al., *Opioid analgesics and antagonists*, Goodman and Gilman's: The Pharmacological Basis of Therapeutics, 9th Ed., 1995, Section III Drugs Acting on the Central Nervous System, 23: 521-554.

Root et al., *Septicernia and septic shock*, Part Five of Infectious Diseases, Section 3, Clinical Syndromes, Harrison's Principles of Internal Medicine, 12th Ed., McGraw-Hill, 1991, 502-507.

Schultz, et al.,, *Ischemic Preconditioning and Morphine-Induced Cardioprotection Involve the Delta -opioid Receptor In the Intact Rat Heart*, Mol Cell Cardiol 29. 2187-2195 (1997).

Schultz et al., *Ischemic preconditioning in the intact rat heart is mediated by δ1- but not μor X-opioid recptors*, Circ 97:1282-1289, 1998.

Schultz et al., *Evidence for Involvement of opioid receptors in ischemic preconditioning in rat hearts*, Am, J. Physiol. 268 (Heart Circ. Physiol, 3): H2157-H2161, 1995.

Schultz et al., *Morphine mimics the cardioprotective effect of Ischemic preconditioning via a glibendamide-sensitive mechanism in the rat heart*, Circ, Research. 78: 1100-1104, 1996.

Schulz et al., *Involvement of activation of ATP-dependent potassium channels in ischemic preconditioning in swine*, Am. J. Physiol. 267: H1341-1352, 1994.

Schwartz et al., *Delta opioid receptors and low temperature myocardial protection*, Ann. Thorac. Surg. 68; 2089-92, 1999.

Stefano et al., *Delta-2 opioid receptor subtype on human vascular endothellum uncouples morphione stimulated nitric oxide release*, Internatoinal J. Cardiology 64: Suppl. 1, S43-S51, 1998.

Thomas et al., *Structure-sctivity relationships of a series of D-Ala2-deltorphin I and II analogues; In vitro blood-brain barrier permeability and stability*, Journal of Pharmacolopgy and Experieritial Therapy, vol. 281, No. 2: 817-825, 1997.

Thornton, Jr. et al., *Opioid peptides and primary biliary clrrhosis*, BMJ, vol. 297, No. 6662: 1501-4, 1988.

Toombs et al., *Limitation of infarct size in the rabbit by Ischaemic proconditioning is reversible with glibenclamide*, Cardio. Res, 27: 617-622, 1993.

Tsutsui et al., *IL-1B accounts for both TNF-α- and fas ligand-mediated hepatotoxic pathways in endotoxin-Induced liver injury in mice*, The Journal of Immunology, 159: 3961-3967, 1997.

VanWinkle et al., *Cardioprotection provided by adenosine receptor activation is abolished by blockade of the K-ATP channel*, Am. J. Physiol. 268: H829-H839, 1994.

Wu et al., *Delta opioid extends hypothermic preservation time of the lung*, J. Thorac. Cardiovasc. Surg. 1996; 111: 259-267.

Zhao and Bhargava, *Effects of multiple intracerebroevntricular injections of [D-Pen2, D-Pen5] enkephalin and [D-Ala2, Glu4] deltorphln II on tolerance to their analgesic action and on brain δ-opiod receptors*, Brain Research: 745 (1997) 243-247.

\* cited by examiner

```
                              SEQUENCE LISTING

<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<221> NAME/KEY: MOD_RES
<222> LOCATION: (1)...(7)
<223> OTHER INFORMATION: Xaa = D-Met; artificial sequence is completely
      synthesized

<400> SEQUENCE: 1

Tyr Xaa Phe His Leu Met Asp
1               5

<210> SEQ ID NO 2
<211> LENGTH: 13
<212> TYPE: PRT
<213> ORGANISM: Artificial Sequence
<220> FEATURE:
<221> NAME/KEY: MOD_RES
<222> LOCATION: (1)...(13)
<223> OTHER INFORMATION: Xaa = D-Ala; artificial sequence is completely
      synthesized

<400> SEQUENCE: 2

Tyr Xaa Phe Gly Tyr Pro Ser Gly Glu Ala Lys Lys Ile
1               5                   10
```

PROTECTION AGAINST ISCHEMIA AND REPERFUSION INJURY

This application is a continuation of U.S. patent application Ser. No. 09/947,656, filed Sep. 6, 2001 now U.S. Pat. No. 6,900,178, which claims benefit of Application Ser. No. 60/232,093, filed Sep. 12, 2000.

FIELD OF THE INVENTION

The invention relates to compounds protective against ischemia and reperfusion injury, particularly in the myocardium, and their use.

BACKGROUND

Tissues deprived of blood and oxygen undergo ischemic necrosis or infarction with possible irreversible organ damage. In some circumstances, however, such as during cardiac surgery, it is desirable to interrupt the normal myocardial contractions (cardioplegia) and actually induce ischemia. Such elective or obligatory ischemia occurs in the presence of safeguards such as cardioplegia-induced cardiac arrest and hypothermia. While these safeguards provide considerable myocardial protection, alteration of myocardial energetics (stunning) and poor postoperative ventricular function still remain significant problems.

Once the flow of blood and oxygen is restored to the organ or tissue (reperfusion), the organ does not immediately return to the normal preischemic state. Reperfused postischemic non-necrotic myocardium is poorly contractile and has reduced concentrations of high energy nucleotides, depressed subcellular organelle function and membrane damage that resolves only slowly. Although reperfusion restores oxygen and reverses ischemia, repletion of high energy nucleotides such as adenosine triphosphate (ATP) and reversal of ischemic membrane damage is slow, and contractile function may be profoundly depressed for a long period. Just minutes of ischemia causes loss of myocardial systolic wall thickening for hours. Longer periods of reversible ischemia may depress contractility for days. Studies confirm that, despite restoration of myocardial flow and a quick recovery of myocardial oxygen consumption ($MVO_2$) following ischemia, there is only very slow recovery of myocardial contractile function. The problems are exacerbated in high risk patients, such as those with poor preoperative ventricular function, recent myocardial infarction or left ventricular hypertrophy. These same problems also occur during organ storage for cardiac transplant, under which there are time constraints due to the limits of myocardial preservation.

Postischemic dysfunction may be due to a variety of factors. Oxygen free radicals may play a role, as generation of free radicals in stunned myocardium has been demonstrated and free radical scavengers have been shown to attenuate contractile dysfunction. Impaired intracellular calcium handling and calcium overload during early reperfusion may contribute to postischemic dysfunction; while calcium infusions enhance contractility in both normal and postischemic myocardium, ischemia as short as a few minutes produces an impairment in sarcoplasmic reticulum calcium transport and a shift of the calcium ATPase activity. Postischemic myocardium is also associated with reduced concentrations of myocardial high-energy phosphates and adenine nucleotides, as obligatory reduction in myocardial ATP content during ischemia occurs as myocytes utilize ATP for maintenance of cellular integrity. Since ATP is essential for myocardial contraction and relaxation, ATP depletion may have detrimental effects upon postischemic myocardial functional recovery.

The high volume of cardiac-related surgeries, both elective and emergency procedures and including cardiac transplants, lead to the above-described problems. Thus, methods and agents to provide protection against myocardial ischemia and to avoid post ischemic dysfunction are needed.

SUMMARY OF THE INVENTION

The invention is directed to agents and a method of using the agents to reduce the injury associated with ischemia and reperfusion of organs such as the heart. The compounds are Tyr-D-Met-Phe-His-Leu-Met-Asp-$NH_2$ SEQ ID NO:1, hereinafter referred to as Deltorphin A, and Tyr-D-Ala-Phe-Gly-Tyr-Pro-Ser-Gly-Glu-Ala-Lys-Lys-Ile SEQ ID NO:2, hereinafter referred to as Dermorphin H. Administration of Deltorphin A SEQ ID NO:1 and Dermorphin H SEQ ID NO:2, particularly prior to an ischemic event, reduces tissue necrosis and preserves organ function.

In one embodiment, a method of protecting against ischemia and reperfusion injury in a mammal is disclosed. An effective concentration of Deltorphin A SEQ ID NO:1 or Dermorphin H SEQ ID NO:2 is administered to the mammal in a pharmaceutically acceptable formulation prior to the onset of ischemia, for example, 24 hours prior to ischemia. In other embodiments, Deltorphin A SEQ ID NO:1 or Dermorphin H SEQ ID NO:2 is administered substantially concurrently with the onset of ischemia, during an ischemic episode, or post-ischemia. The formulation may be administered parenterally at a concentration in the range of about 1–20 mg/kg of body weight.

The invention is also directed to a method to prevent damage to an isolated organ, for example, a heart for transplant. The isolated organ is exposed to a preservative solution containing an effective amount of Deltorphin A SEQ ID NO:1 or Dermorphin H SEQ ID NO:2. The concentration of Deltorphin A SEQ ID NO:1 or Dermorphin H SEQ ID NO:2 in the preservative solution for a heart is about 100 µM.

The invention is additionally directed to a method for reducing effects of an ischemic episode in a mammal by administering an effective concentration of Deltorphin A SEQ ID NO:1 or Dermorphin H SEQ ID NO:2 in a pharmaceutically acceptable carrier. Administration is prior to or substantially concurrently with the onset of ischemia, or one hour post cerebral ischemia.

The invention is further directed to a composition that protects a mammalian organ from injury. The composition contains Deltorphin A SEQ ID NO:1 or Dermorphin H SEQ ID NO:2, in either a naturally occurring form or a synthesized form.

The invention is also directed to an organ preservative solution that contains Deltorphin A SEQ ID NO:1 or Dermorphin H SEQ ID NO:2 at a concentration effective to protect the organ, such as a heart, from ischemic injury.

These and other advantages of the invention will be apparent in light of the following drawings and detailed description.

DETAILED DESCRIPTION

Figure 1:
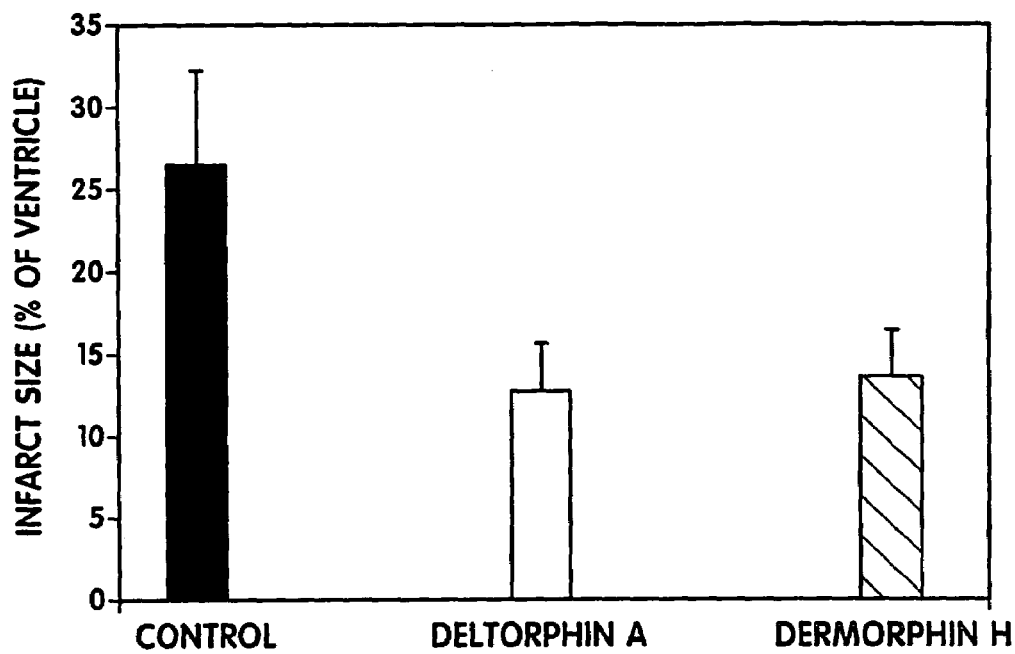
FIG. 1 is a histogram showing myocardial infarction size in control and treated animals.

The invention is directed to compounds that have a salutary effect on cardiac function following ischemia, and methods of using the compounds. The compounds may be administered directly to an individual, and are particularly effective when administered 24 h prior to the onset of ischemia. This may occur, for example, prior to scheduled cardiac surgery. The compounds may also be included in a preservative solution for an isolated organ, such as a heart or liver being maintained viable for transplant.

One of the compounds is a heptapeptide having the sequence Tyr-D-Met-Phe-His-Leu-Met-Asp-NH$_2$ SEQ ID NO:1, hereinafter referred to as deltorphin A. Another of the compounds is a thirteen amino acid sequence Tyr-D-Ala-Phe-Gly-Tyr-Pro-Ser-Gly-Glu-Ala-Lys-Lys-Ile SEQ ID NO:2. The peptides may be produced by a number of methods, such as using an automated peptide synthesizer, through recombinant molecular techniques, or isolated from a naturally occurring source, as is known to one skilled in the art. Deltorphin A SEQ ID NO:1 has a molecular weight of 955.1 daltons, and Dermorphin H SEQ ID NO:2 has a molecular weight of about 1430.64 daltons. Both Deltorphin A SEQ ID NO:1 and Dermorphin H SEQ ID NO:2 are insoluble in water or saline, but may be solubilized by adding 100 µM of a solution comprised of ethanol, propylene glycol, and 1 N NaOH in a 1:1:1 ratio, with sterile physiological saline then used to obtain the appropriate concentration. The initial alkaline pH is adjusted to 7.4 with 1 N HCl.

Deltorphin A SEQ ID NO:1 and Dermorphin H SEQ ID NO:2 that have been solubilized may be administered by parenteral means, for example, by intravenous injection. In one embodiment, administration of Deltorphin A SEQ ID NO:1 is at the time of induced ischemia, but may also be added during or even after an ischemic event. For administration into a mammal, a dose of about 1–20 milligrams per kilogram (mg/kg) is useful. For administration into a tissue or organ preservation solution, a concentration of about 100 µM is useful.

Deltorphin A SEQ ID NO:1 and Dermorphin H SEQ ID NO:2 may be administered directly into a mammal, either alone or in combination with other substances. Alternatively, it may be added as a component of a solution used to maintain the viability of isolated organs, such as an additive to cardioplegia and other organ preservation solutions. In one embodiment, Deltorphin A SEQ ID NO:1 and/or Dermorphin H SEQ ID NO:2 is coadministered as an adjuvant with other compounds or strategies that are designed to protect organs from ischemia. As an example, Deltorphin A SEQ ID NO:1 and/or Dermorphin H SEQ ID NO:2 may be administered with agents that affect nitric oxide (NO) synthase, such as arginine hydrochloride. Arginine hydrochloride is known to prevent the decline in cardiac function following an ischemic episode.

The following description demonstrates use and efficacy of Deltorphin A SEQ ID NO:1 and Dermorphin H SEQ ID NO:2 in a variety of systems.

Perfused Heart

Deltorphin A SEQ ID NO:1 or Dermorphin H SEQ ID NO:2, at a dose of 2 mg/kg and solubilized as described above, was administered by tail vein injection into rats weighing between about 350–400 g (number of animals (n)=6). Control rats (n=6) were injected in the same manner with an equal volume of 0.9% NaCl. After 24 h, the hearts from both treated and control animals were excised and perfused in a modified Langendorff perfusion apparatus at 37° C. using oxygenated Krebs-Henseleit buffer as the perfusate, as known to one skilled in the art. Coronary perfusion pressure was maintained at 700 mm Hg by regulating coronary flow. All hearts were paced at 5.5 Hz (300 beats per minute, bpm) except during ischemia. A saline-filled balloon was inserted in the left ventricle to measure developed pressure (DP) and end-diastolic pressure (EDP) in mm Hg. After 15 min equilibration, both groups were subjected to 20 min zero-flow global ischemia, and then were reperfused for 120 min.

Left ventricles were isolated and divided into three segments along their short axis, stained with triphenyltetrazolium chloride, and stored in formalin. Infarct size was measured on digitized images and expressed as a percentage of myocardium. Data were expressed as mean plus or minus standard error of the mean (±SEM) and were analyzed using a paired Student's t-Test. Confidence limits were established at 95%.

The results are shown in FIG. 1, which is a histogram of the infarct size in hearts from animals receiving only saline (control, solid bar), in animals treated with Deltorphin A SEQ ID NO:1 at 2.0 mg/kg (treated, open bar) 24 h prior to 20 min ischemia and 120 min reperfusion, and animals treated with Dermorphin H SEQ ID NO:2 at 2.0 mg/kg (treated, hatched bar) 24 h prior to 20 min ischemia and 120 min reperfusion. Pretreatment of animals with Deltorphin A SEQ ID NO:1 or Dermorphin H SEQ ID NO:2 decreased the percent of infarct size. Control rats had a mean infarct size of 27±5%, while rats pretreated with Deltorphin A SEQ ID NO:1 had a reduced mean infarct size of 12.95±3.3%, and rats pretreated with Dermorphin H SEQ ID NO:2 had a reduced mean infarct size of 13.5±3.5%.

Specific infarct volumes in four separate cross sectional areas of brains isolated from animals treated post-ischemia with Deltorphin A SEQ ID NO:1 and Dermorphin H SEQ ID NO:2 are shown in Tables 1–3. In each case, six male mice (strain C57) were subjected to ischemia for one hour and then received an injection of either 100 µl normal saline (vehicle), 100 µl of 4.0 mg/kg Deltorphin A SEQ ID NO:1 (Table 2), or 100 µl of 4.0 mg/kg Dermorphin H SEQ ID NO:2 (Table 3). The dose of Deltorphin A SEQ ID NO:1 and Dermorphin H SEQ ID NO:2 may be in the range of 1 mg/kg to 4 mg/kg. Reperfusion followed for 24 hours, then animals were sacrificed and 2 mm brain sections from each of four areas were evaluated. The total cross section area is the sum of the four cross section areas; likewise, the total damaged cross section areas is the sum of the four damaged cross section areas for each animal.

TABLE 1

| Saline (Vehicle) Treated | | | | | | |
|---|---|---|---|---|---|---|
| Cross Section Area 1 | 14.81 | 14.65 | 12.55 | 13.18 | 15.35 | 15.9 |
| Cross Section Area 2 | 22.52 | 22.39 | 19.52 | 20.68 | 22.08 | 20.22 |
| Cross Section Area 3 | 25.24 | 25.45 | 21.84 | 23.51 | 24.77 | 22.69 |
| Cross Section Area 4 | 24.51 | 24.05 | 21.54 | 24.98 | 23.81 | 22.73 |
| Total Cross Section Area | 87.08 | 86.54 | 75.45 | 82.35 | 86.01 | 81.54 |
| Damaged Cross Section Area 1 | 6.58 | 4.49 | 5.77 | 5.02 | 4.83 | 5.86 |
| Damaged Cross Section Area 2 | 9.7 | 6.86 | 7.42 | 8.21 | 8.81 | 6.57 |
| Damaged Cross Section Area 3 | 11.86 | 10.7 | 10.65 | 11.79 | 9.52 | 8.24 |
| Damaged Cross Section Area 4 | 10.02 | 12.22 | 11.03 | 11.21 | 10.26 | 10.76 |
| Total Damaged Cross Section Area | 38.16 | 34.27 | 34.87 | 36.23 | 33.42 | 31.43 |
| Damaged % | 43.82 | 39.60 | 46.22 | 44.00 | 38.86 | 38.55 |
| Corrected Volume | 87.644 | 68.54 | 69.74 | 72.46 | 66.84 | 62.86 |

For animals receiving only saline after one hour of ischemia, the infarct volume was about 42% (total damaged cross section area of 208.38, total cross section area of 498.97, 208.38/498.97=0.417). The corrected volume was obtained by multiplying the damaged cross section area by 2, since 2 mm sections were assessed. In all six control animal this was 428.08, yielding an average infarct volume of 71.35 mm³ (428.08/6), with a standard deviation of ±8.598.

TABLE 2

| Deltorphin A Treated | | | | | | |
|---|---|---|---|---|---|---|
| Cross Section Area 1 | 16.42 | 15 | 13.89 | 14.67 | 15.23 | 14.56 |
| Cross Section Area 2 | 22.07 | 22.81 | 20.06 | 21.23 | 20.78 | 21.34 |
| Cross Section Area 3 | 24.17 | 25.51 | 23.52 | 23.79 | 24.14 | 24.56 |

TABLE 2-continued

| Deltorphin A Treated | | | | | | |
|---|---|---|---|---|---|---|
| Cross Section Area 4 | 20.77 | 23.49 | 23.24 | 21.55 | 22.34 | 20.98 |
| Total Cross Section Area | 83.43 | 86.81 | 80.71 | 81.24 | 82.49 | 81.44 |
| Damaged Cross Section Area 1 | 5.16 | 4.14 | 5.09 | 4.98 | 5.32 | 4.76 |
| Damaged Cross Section Area 2 | 7.48 | 5.86 | 7.7 | 6.97 | 7.36 | 6.83 |
| Damaged Cross Section Area 3 | 3.69 | 3.26 | 9.49 | 8.59 | 9.23 | 8.75 |
| Damaged Cross Section Area 4 | 3.77 | 3.4 | 7.36 | 6.74 | 6.94 | 7.11 |
| Total Damaged Cross Section Area | 20.1 | 16.66 | 29.64 | 27.28 | 28.85 | 27.45 |
| Damaged % | 24.09 | 19.19 | 36.72 | 33.58 | 34.97 | 33.71 |
| Corrected Volume | 40.2 | 33.32 | 59.28 | 54.56 | 57.7 | 54.9 |

For animals receiving Deltorphin A after one hour of ischemia, the infarct volume was reduced to about 30% (total damaged cross section area of 149.98, total cross section are of 496.12, 149.98/496.12=0.302). In all six Deltorphin A treated animals, the corrected volume was 299.96, yielding an infarct volume of 49.99 mm³ (299.96/6), with a standard deviation of ±10.63.

TABLE 3

| Dermorphin H Treated | | | | | | |
|---|---|---|---|---|---|---|
| Cross Section Area 1 | 14.92 | 13.87 | 14.94 | 14.65 | 13.69 | 14.27 |
| Cross Section Area 2 | 22.62 | 21.52 | 21.48 | 22.33 | 21.66 | 21.36 |
| Cross Section Area 3 | 23.5 | 23.8 | 23.69 | 23.98 | 23.71 | 22.35 |
| Cross Section Area 4 | 23.8 | 21.24 | 21.59 | 21.87 | 22.43 | 23.39 |
| Total Cross Section Area | 84.84 | 80.43 | 81.7 | 82.83 | 81.49 | 81.37 |
| Damaged Cross Section Area 1 | 4.5 | 5.24 | 3.76 | 4.25 | 3.99 | 3.47 |
| Damaged Cross Section Area 2 | 5.41 | 6.75 | 5.2 | 7.13 | 5.87 | 5.13 |

TABLE 3-continued

| | | | Dermorphin H Treated | | | |
|---|---|---|---|---|---|---|
| Damaged Cross Section Area 3 | 6.43 | 7.34 | 4.82 | 6.77 | 6.22 | 5.36 |
| Damaged Cross Section Area 4 | 3.45 | 3.23 | 3.37 | 4.62 | 4.15 | 3.89 |
| Total Damaged Cross Section Area | 19.79 | 22.56 | 17.15 | 22.77 | 20.23 | 17.85 |
| Damaged % | 23.33 | 28.05 | 20.99 | 27.49 | 24.83 | 21.94 |
| Corrected Volume | 39.58 | 45.12 | 34.3 | 45.54 | 40.46 | 35.7 |

For animals receiving Dermorphin H after one hour of ischemia, the infarct volume was reduced to about 24% (total damaged cross section area of 120.35, total cross section are of 492.66, 120.35/492.66=0.244. In all six Dermorphin H treated animals, the corrected volume was 240.7, yielding an infarct volume of 40.12 mm$^3$ (240.7/6), with a standard deviation of 4.652.

These results are summarized as follows.

| Treatment | Average Infarct Volume (mm$^3$) | Standard Deviation | Infarct Volume |
|---|---|---|---|
| Control | 71.35 | 8.598 | 42% |
| Deltorphin A | 49.99 | 10.63 | 30% |
| Dermorphin H | 40.12 | 4.652 | 24% |

The data demonstrate the efficacy of Deltorphin A and Dermorphin H treatment post cerebral ischemia.

Figure 2:
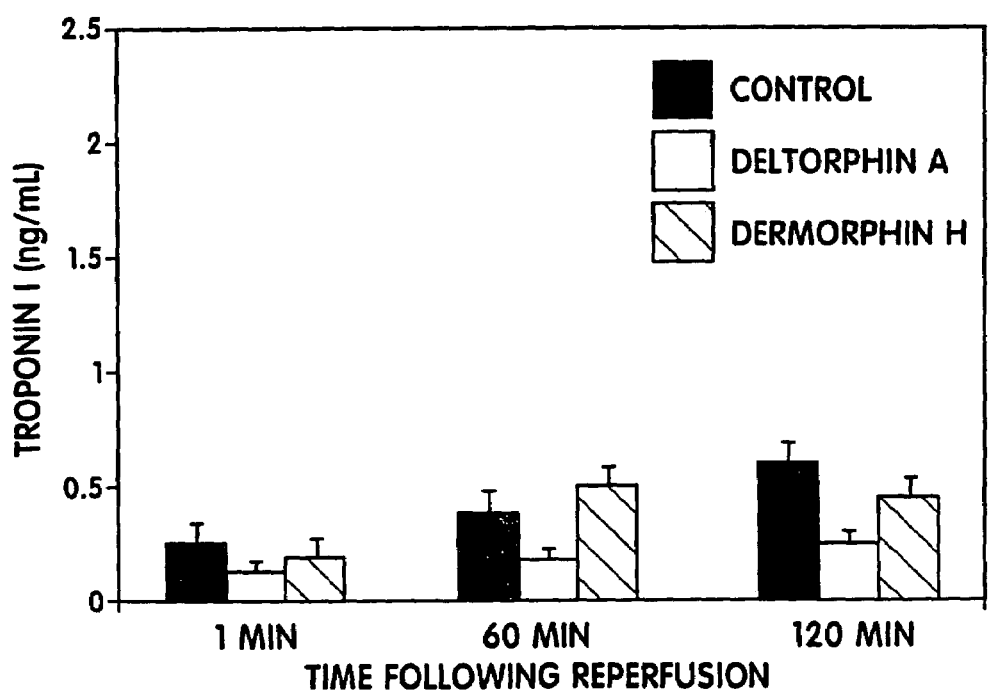
FIG. 2 is a histogram showing post-ischemic release of troponin I in control and treated animals.

Pretreatment with Deltorphin A SEQ ID NO:1 and Dermorphin H SEQ ID NO:2 also significantly decreased the cardiac form of troponin I (cTn-1) values following 20 min ischemia, as shown in FIG. 2. An increase in cTn-1, a protein associated specifically with the cardiac muscle, indicates myocardial damage, likewise, a decrease in cTn-1 indicates less cardiac damage.

Figure 3:
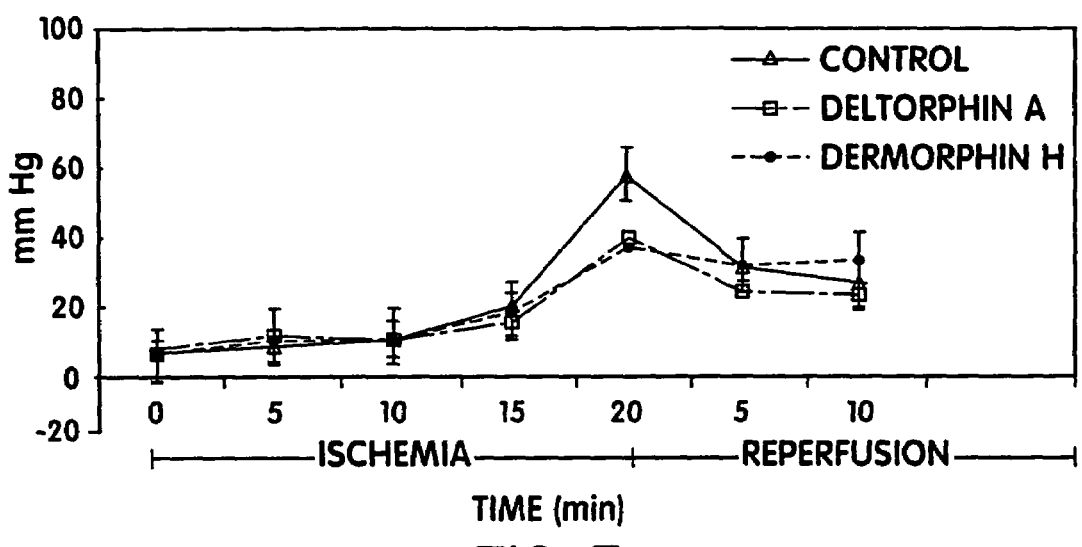
FIG. 3 is a graph showing end diastolic pressure in the left ventricle of control and treated animals.

FIG. 3 is a histogram showing cTn-1 released during reperfusion of isolated hearts after 20 min ischemia in rats treated 24 h prior to ischemia with 0.5 ml saline (control), 2.0 mg/kg Deltorphin A SEQ ID NO:1, and 2.0 ml/kg Dermorphin H SEQ ID NO:2. The solid bars represent control animals (n=6), the open bars represent Deltorphin A SEQ ID NO:1 treated animals (n=6), and the hatched bars represent Dermorphin H SEQ ID NO:2 treated animals (n=6). At time points during reperfusion where samples were collected for cTn-1 analysis (1, 60, and 120 min reperfusion), Tn-1 levels in control rats were significantly higher than Tn-1 levels in Deltorphin A SEQ ID NO:1 treated rats at 1 min and 60 minutes following reperfusion, and were also higher at 120 min following reperfusion. Tn-1 levels in control rats were higher than Tn-1 levels in Dermorphin H SEQ ID NO:2 treated rats at 1 minute and 120 minutes following reperfusion. This data indicated that pretreatment with Deltorphin A SEQ ID NO:1 and Dermorphin H SEQ ID NO:2 decreased the damage to the myocardium, as compared to untreated animals.

Figure 4:
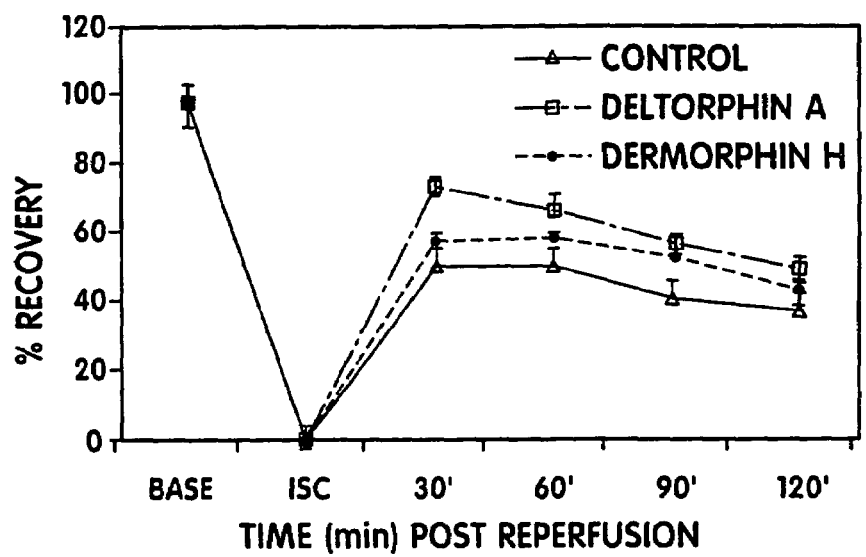
FIG. 4 is a graph showing functional recovery in control and treated animals.

Deltorphin A SEQ ID NO:1 and Dermorphin H SEQ ID NO:2 pretreatment also resulted in improved postischemic ventricular function. FIG. 3 is a graph of end diastolic pressure in mm/Hg in the left ventricle (LVEDP) during reperfusion of isolated rat hearts after 20 min ischemia in rats pretreated 24 h prior to ischemia with 2.0 mg/kg Deltorphin A SEQ ID NO:1 or 2.0 mg/kg Dermorphin H SEQ ID NO:2. Open squares are from treated animals, and solid circles are from animals treated with 0.5 ml saline (control). FIG. 4 is a graph showing percent of functional recovery during reperfusion of isolated rat hearts after 20 min ischemia in rats treated 24 h prior to ischemia with 2.0 mg/kg Deltorphin A SEQ ID NO:1 or 2.0 mg/kg Dermorphin H SEQ ID NO:2. Open squares are from treated animals, and solid circles are from control animals. Differences in recovery of developed pressure (DP) in hearts from Deltorphin A SEQ ID NO:1 and Dermorphin H SEQ ID NO:2 treated animals remained lower following the initiation of reperfusion, as shown in FIG. 3. As shown in FIG. 4, left ventricular functional recovery (% recovery of baseline preischemic developed pressure during reperfusion) for animals treated with 2 mg/kg Deltorphin A SEQ ID NO:1 was significantly increased over control animals up to 120 min following reperfusion (p=0.01). Left ventricular functional recovery for animals treated with Dermorphin-H SEQ ID NO:2 (2.0 mg/kg) was also increased over control animals up to 120 min post reperfusion, but the increase was not statistically significant.

Figure 5:
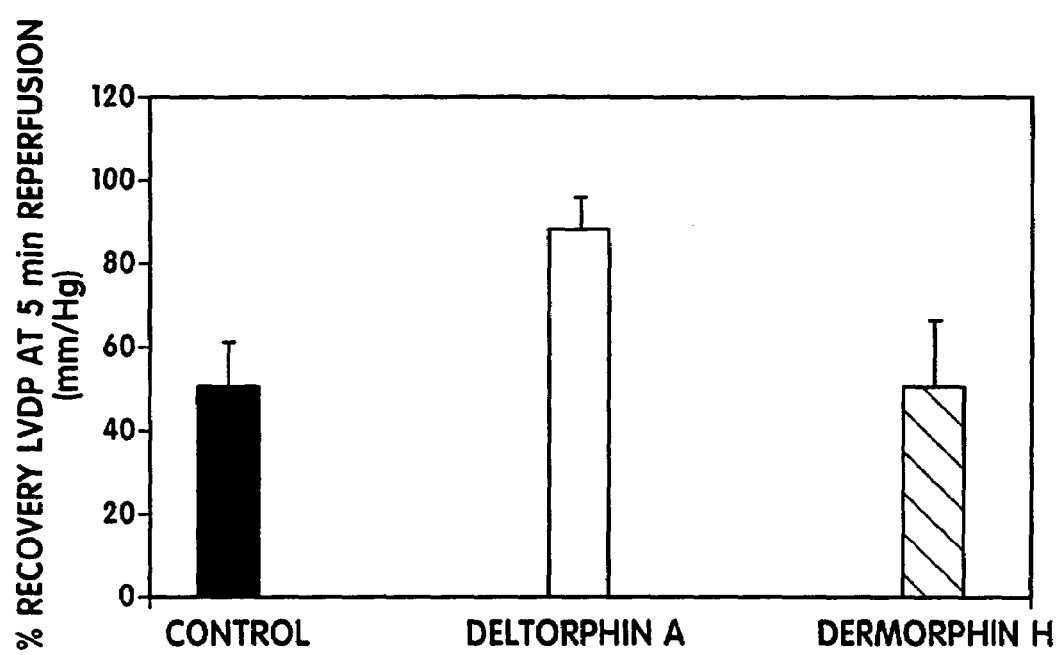
FIG. 5 is a histogram showing ventricular functional recovery in control and treated animals.

As shown in FIG. 5, left ventricular functional recovery was significantly improved in Deltorphin A SEQ ID NO:1 treated animals (about 85%) (open bar) compared to control animals (about 51%) (solid bar) at 5 min of reperfusion, while left ventricular functional recovery in Dermorphin H SEQ ID NO:2 treated animals and control animals was about the same (about 51%).

These results show that in a normoxic, isolated perfused rat heart preparation, administration of Deltorphin A SEQ ID NO:1 and Dermorphin H SEQ ID NO:2 confers cardioprotection when administered either prior to planned ischemia or post ischemia. The salutary effects on the post-ischemic myocardium include reduced infarct size, reduced infarct volume, decreased release of cardiospecific troponin I, and improved ventricular performance.

As another benefit, Deltorphin A SEQ ID NO:1 and Dermorphin H SEQ ID NO:2 may provide a benefit in protecting against arrhythmias, similar to the effect of the δ-opioid receptor agonist TAN-67, as reported by Fryer et al. in 274 *J. Biol. Chem.* 451–457, 2000, which is expressly incorporated by reference herein in its entirety.

The invention in its broader aspects is therefore not limited to the specific details, representative apparatus and method, and illustrative examples shown and described. Accordingly, departures may be made from such details without departing from the spirit or scope of applicant's general inventive concept.

What is claimed is:

1. A composition comprising a compound that affects nitrogen oxide (NO synthase) and at least one of Deltorphin A, SEQ ID No: 1, or Dermorphin H, SEQ ID No: 2, in a pharmaceutically acceptable formulation, wherein said compound that affects NO synthase is arginine hydr